United States Patent
Nakatani et al.

(10) Patent No.: US 8,699,032 B2
(45) Date of Patent: Apr. 15, 2014

(54) SURFACE PLASMON RESONANCE SENSOR, LOCALIZED PLASMON RESONANCE SENSOR, AND METHOD FOR MANUFACTURING SAME

(75) Inventors: Masaya Nakatani, Hyogo (JP); Takeki Yamamoto, Hyogo (JP)

(73) Assignee: Panasonic Corporation, Osaka (JP)

( * ) Notice: Subject to any disclaimer, the term of this patent is extended or adjusted under 35 U.S.C. 154(b) by 419 days.

(21) Appl. No.: 13/142,491

(22) PCT Filed: Jan. 25, 2010

(86) PCT No.: PCT/JP2010/000385
§ 371 (c)(1),
(2), (4) Date: Jun. 28, 2011

(87) PCT Pub. No.: WO2010/087142
PCT Pub. Date: Aug. 5, 2010

(65) Prior Publication Data
US 2011/0267621 A1    Nov. 3, 2011

(30) Foreign Application Priority Data

Jan. 27, 2009  (JP) ................... 2009-014968
Apr. 23, 2009  (JP) ................... 2009-104971

(51) Int. Cl.
*G01N 21/55* (2006.01)
(52) U.S. Cl.
USPC .......................................................... 356/445
(58) Field of Classification Search
USPC .......................................................... 356/445
See application file for complete search history.

(56) References Cited

U.S. PATENT DOCUMENTS

| | | |
|---|---|---|
| 2003/0113231 A1 | 6/2003 | Karube et al. |
| 2008/0037022 A1 | 2/2008 | Nishikawa et al. |
| 2009/0032735 A1 | 2/2009 | Misawa et al. |

FOREIGN PATENT DOCUMENTS

| | | |
|---|---|---|
| JP | 05-052740 A | 3/1993 |
| JP | 05-232537 A | 9/1993 |
| JP | 2001-337036 A | 12/2001 |
| JP | 2004-521323 A | 7/2004 |
| JP | 2007-501432 A | 1/2007 |
| JP | 2007-255947 A | 10/2007 |
| JP | 2008-203187 A | 9/2008 |
| WO | WO 02/44412 A1 | 6/2002 |
| WO | WO 2005/015185 A1 | 2/2005 |
| WO | WO 2005/078415 A1 | 8/2005 |
| WO | WO 2006/098446 A1 | 9/2006 |

OTHER PUBLICATIONS

International Search Report for Application No. PCT/JP2010/000385, Apr. 6, 2010, Panasonic Corporation.
Reuven Gordon, "Surface Plasmon Nanophotonics: A Tutorial," IEEE Nanotechnology Magazine, Sep. 2008, pp. 12-18.

*Primary Examiner* — Michael A Lyons
*Assistant Examiner* — Rebecca C Bryant
(74) *Attorney, Agent, or Firm* — RatnerPrestia

(57) ABSTRACT

A surface plasmon resonance sensor includes a substrate, a dielectric film having a nonlinear optical effect on a first surface of the substrate, and a probe fixed to the dielectric film. A plasmon resonance is produced by resonating a surface plasmon generated on the first surface of the substrate with an evanescent wave generated on a second surface of the substrate by incident light radiated to the second surface. The plasmon resonance is detected by measuring a change of a component of light reflected on the second surface of the substrate. The component of the reflected light is caused by the nonlinear optical effect. This surface plasmon resonance sensor has a high measuring sensitivity.

7 Claims, 13 Drawing Sheets

SURFACE PLASMON RESONANCE SENSOR, LOCALIZED PLASMON RESONANCE SENSOR, AND METHOD FOR MANUFACTURING SAME

This Application is a U.S. National Phase Application of PCT International Application PCT/JP2010/000385.

TECHNICAL FIELD

The present invention relates to a surface plasmon resonance sensor and a localized plasmon resonance sensor using plasmon resonance, and also relates to a method of manufacturing the plasmon sensors.

BACKGROUND ART

A conventional surface plasmon resonance sensor disclosed in Patent Literature 1 includes a prism, a metal film deposited on a bottom surface of the prism, and a probe fixed onto the metal film.

When light enters into the prism under a condition of total reflection, an evanescent wave develops on a surface opposite to the reflecting surface of the metal film, and is coupled with surface plasmon on the metal film. At this moment, a resonance occurs between the evanescent wave and the surface plasmon when a wave number of a component perpendicular to an interface of p-polarized light of the evanescent wave is in consonance with a wave number of the surface plasmon, and an intensity of electric field on the surface of the metal film increases. This results in absorption of the light, which reduces an intensity of reflected light leaving the prism in spite of the condition of total reflection.

The wave number of the surface plasmon depends upon a dielectric constant on the surface of the metal film and a refractive index of a medium contacting the metal. Therefore, changes occur in a wavelength (i.e., resonant wavelength) of the incident light and an incident angle (i.e., a resonance angle) that are the condition of resonance when an object substance is coupled with a probe provided on the metal film.

It is thus possible to analyze the object substance according to a change in relation between the resonant wavelength and reflectivity or a change in relation between the resonance angle and the reflectivity due to the presence or absence of the object substance.

A conventional localized plasmon resonance sensor disclosed in Patent Literature 2 includes plural metal particles arranged on a substrate at constant intervals. When light is radiated to these metal particles and causes a resonant vibration of free electrons in the metal particles with a vibrating frequency of electric field of the light, plasmon excitation occurs around the surfaces of the metal particles. The condition of localized plasmon resonance in this state is determined by the size of the metal particles and a dielectric constant around the particles. In a resonant frequency of the localized plasmon resonance, there emerges a peak of light absorption.

When an antibody coupled specifically with an antigen probe fixed to the metal particles is introduced to the sensor, a dielectric constant of the surfaces of the metal particles changes due to the coupling of the antibody with the antigen probe, hence changing the condition of the localized plasmon resonance. Accordingly, a reaction of the antibody, an object substance with the antigen probe can be sensed by detecting a change of an optical response of the metal particles. The optical response includes fluorescence, Raman scattering, and harmonic luminescence.

The conventional surface plasmon resonance sensor and the conventional localized plasmon resonance sensor exhibit only small changes in the reflectivity under the resonance condition, thus being prevented from having a high sensitivity.

CITATION LIST

Patent Literature 1: Japanese Patent Laid-Open Publication No. 2001-337036
Patent Literature 2: WO2006/098446

SUMMARY OF INVENTION

A surface plasmon resonance sensor includes a substrate, a dielectric film having a nonlinear optical effect on a first surface of the substrate, and a probe fixed to the dielectric film. A plasmon resonance is produced by resonating a surface plasmon generated on the first surface of the substrate with an evanescent wave generated on a second surface of the substrate by incident light radiated to the second surface. The plasmon resonance is detected by measuring a change of a component of light reflected on the second surface of the substrate. The component of the reflected light is caused by the nonlinear optical effect.

This surface plasmon resonance sensor has a high measuring sensitivity.

DETAIL DESCRIPTION OF PREFERRED EMBODIMENTS

Exemplary Embodiment 1

Figure 1:
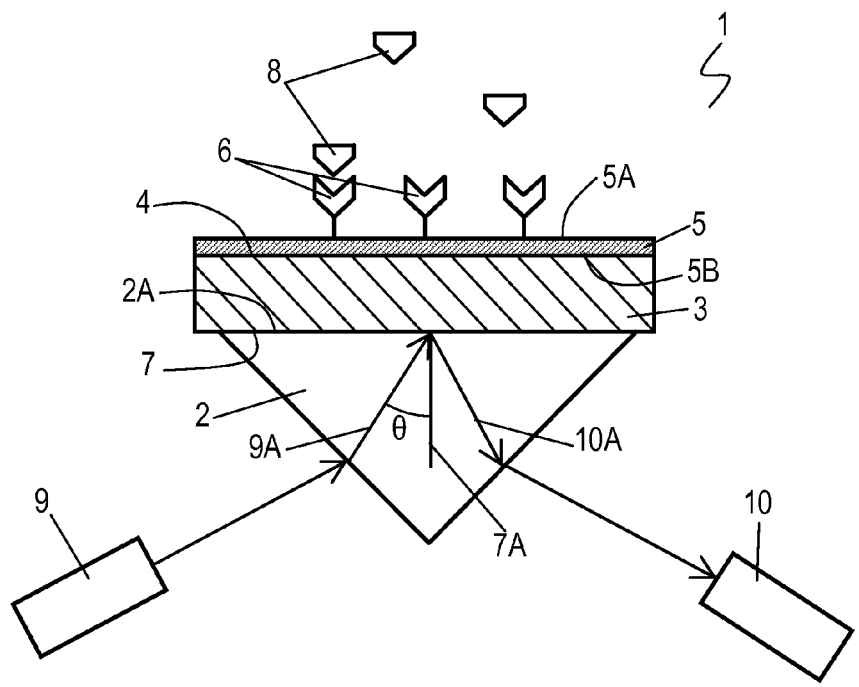
FIG. 1 is a schematic sectional view of a surface plasmon resonance sensor according to Exemplary Embodiment 1 of the present invention.

FIG. 1 is a sectional view of surface plasmon resonance sensor 1 according to Exemplary Embodiment 1 of the present invention. Surface plasmon resonance sensor 1 includes prism 2 made of glass, substrate 3 formed on surface 2A of prism 2, dielectric film 5 formed on substrate 3, and probe 6 fixed onto dielectric film 5. Substrate 3 is made of platinum, and has first surface 4 and second surface 7 opposite to first surface 4. Second surface 7 of substrate 3 is situated on surface 2A of prism 2. First surface 4 of substrate 3 is situated on surface 5B of dielectric film 5. Dielectric film 5 is made of lead zirconate titanate (PZT), and has surface 5A opposite to surface 5B. Probe 6 is disposed on surface 5A of dielectric film 5, and is a functional molecule that reacts specifically with object substance 8. In surface plasmon resonance sensor 1 according to Embodiment 1, object substance 8 is a specific antibody, and probe 6 is an antigen that reacts to and is coupled with the antibody.

Substrate 3 has a thickness of about 40 nm, and dielectric film 5 has a thickness ranging from several nanometers to 10 nm. Substrate 3 can be formed by any method, such as a vacuum deposition method or a sputtering method.

Substrate 3 is made of material that can generate surface plasmon on first surface 4 and that is preferably metal, such as platinum or gold. According to Embodiment 1, substrate 3 is made of platinum, and has a lattice constant close to that of dielectric film 5 made of PZT. This arrangement improves crystallinity of dielectric film 5, further increasing a nonlinear optical effect.

Dielectric film 5 is made of dielectric material having a nonlinear optical effect. The dielectric material of dielectric film 5 preferably has a very high nonlinear optical effect, and is lead perovskite-type material according to Embodiment 1.

Surface plasmon resonance sensor 1 according to Embodiment 1 further includes light projector 9 for radiating light 9A having frequency ω to second surface 7 of substrate 3, and measuring device 10 for measuring the intensity of light 10A reflected on second surface 7. Light 9A radiated from light projector 9 reaches second surface 7 at an incident angle θ. The incident angle θ is an angle formed between normal line 7A of second surface 7 and light 9A. Measuring device 10 specifically measures an intensity of a component having frequency 2ω out of components of light 10A reflected on second surface 7. The component having frequency 2ω is a second-order harmonic component of light 9A having frequency ω. Since the incident light enters dielectric film 5 from first surface 4 of substrate 3, dielectric film 5 is not necessarily made of transparent material allowing light and electromagnetic wave to pass through the material, but can be made of material having a high nonlinear optical effect, such as lead perovskite-type material or non-lead inorganic nonlinear optical material. Although measuring device 10 can be placed on one side facing second surface 7 of substrate 3 or the other side facing first surface 4 of substrate 3, measuring device 10 is preferably placed on the side facing second surface 7 of substrate 3 to improve sensitivity by preventing dielectric film 5 from attenuating the reflected light. The arrangement of light projector 9 and measuring device 10 placed on the side facing second surface 7 of substrate 3, as shown in FIG. 1, can prevent probe 6 and object substance 8 from attenuating the incident light and the reflected light.

According to Embodiment 1, light projector 9 includes a semiconductor laser projector for generating a laser beam. However, it needs not be limited to a laser beam, but any other form of light 9A can be used such as an electromagnetic wave having a wavelength outside of the light spectrum.

A method of measuring the reaction between probe 6 and object substance 8 of surface plasmon resonance sensor 1 according to Embodiment 1 will be described below.

Surface plasmon resonance sensor 1 according to Embodiment 1 measures the reaction by measuring dependency of the intensity of the second-order harmonic component of reflected light 10A against an incident angle with using a secondary nonlinear optical effect. Here, the second-order harmonic is a component having frequency 2ω for incident light 9A having frequency ω.

First, a rotary stage and prism 2 are mounted onto a sample holder of a fluorescence spectrometer. Light projector 9 radiates light 9A to second surface 7 of substrate 3 located on surface 2A of prism 2 under the condition of total reflection. Light 9A is p-polarized light that has an electric field perpendicular to second surface 7 of substrate 3.

Incident light 9A passes through substrate 3 to first surface 4 opposite to second surface 7, and generates an evanescent wave. This evanescent wave is coupled with surface plasmon produced near first surface 4 of substrate 3 contacting dielectric film 5. At this moment, a resonance occurs between the evanescent wave and the surface plasmon when a wave number of a component perpendicular to an interface of the evanescent wave is in consonance with a wave number of the surface plasmon. This resonance increases an electric-field intensity near first surface 4 of substrate 3.

Figure 2:
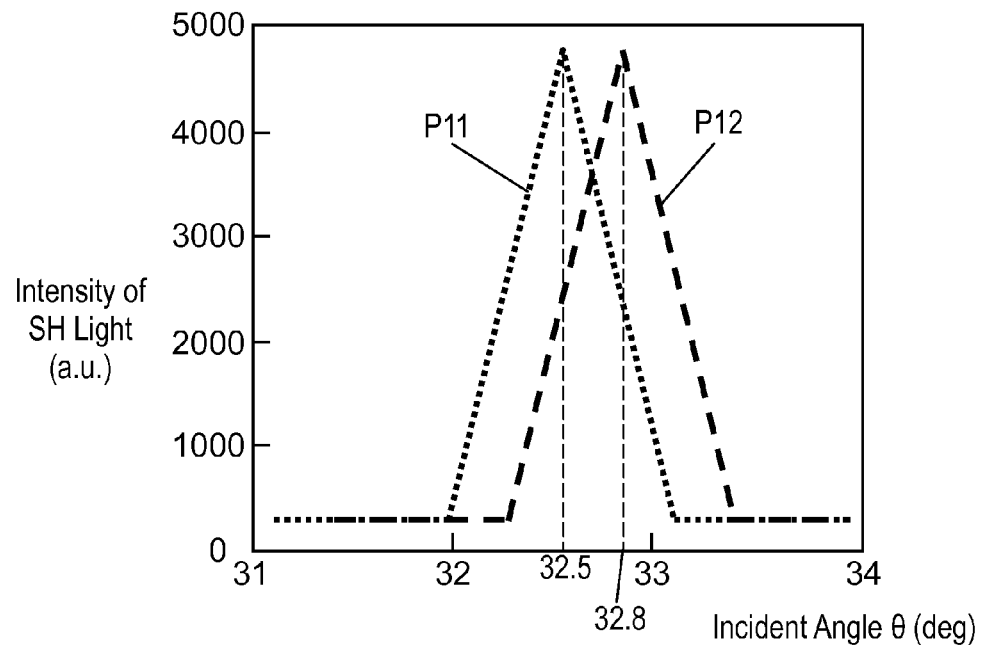
FIG. 2 shows a characteristic of the surface plasmon resonance sensor according to Embodiment 1.

FIG. 2 shows a characteristic of intensity of the second-order harmonic (SH) component of reflected light 10A of surface plasmon resonance sensor 1 according to Embodiments 1. In FIG. 2, the horizontal axis represents incident angle θ, and the vertical axis represents intensity of second-order harmonic (SH) of light 9A. Profile P11 represents the intensity of the SH component at an initial stage before object substance 8 is introduced to surface plasmon resonance sensor 1 thus allowing probe 6 not to be reacted with object substance 8. At the initial stage, surface plasmon resonance occurs near first surface 4 of substrate 3 contacting dielectric film 5 when the incident angle θ is 32.5°, as denoted by profile P11, hence increasing the electric field near first surface 4 of substrate 3. This produces a strong electric field exerted on dielectric film 5 provided on first surface 4 of substrate 3, thereby generating a second-order harmonic wave, which is light having frequency 2ω due to the nonlinear optical effect of dielectric film 5.

Nonlinear polarization of dielectric film 5 increases in proportion to the second power of the electric field intensity of incident light 9A, and the second-order harmonic wave increases in proportion to the fourth power of the electric field intensity. Accordingly, the second-order harmonic wave has the intensity enhanced, accordingly being measured sensitively by measuring device 10. As described, measuring device 10 can assess the resonance sensitively by observing a higher-order component of harmonics of reflected light 10A than the fundamental component of the nonlinear optical effect of reflected light 10A. According to Embodiment 1, surface plasmon resonance sensor 1 exhibits the second-order harmonic wave of very high intensity since dielectric film 5 is made of material having a high nonlinear effect, which is a material that produces intensive nonlinear polarization. According to Embodiment 1, the second-order harmonic wave is enhanced to nearly 1,000 times by the surface plasmon resonance of dielectric film 5, and it shows a highest peak at the incident angle of 32.5°.

Next, object substance 8 is introduced to probe 6 to allow probe 6 to react with object substance 8. A dielectric constant and a refractive index of the surface of dielectric film 5 change when object substance 8 performs an antigen-antibody reaction and is coupled with probe 6. Since a wave number of the surface plasmon of substrate 3 is dependent upon a dielectric constant near first surface 4 of substrate 3 and a refractive index of a medium contacting substrate 3, the condition of developing the surface plasmon resonance changes due to the coupling of object substance 8 with probe 6.

In Embodiment 1, profile P11 changes to profile P12 after the introduction of object substance 8 at the initial stage. According to the profile P12, intensity of the second-order harmonic wave exhibits a highest peak at incident angle θ of 32.8°. In other words, the reaction of object substance 8 with probe 6 can be detected when the incident angle θ that induces the resonance shifts due to the coupling between probe 6 and object substance 8. It is considered that object substance 8 does not react with probe 6 if the incident angle θ which induces the resonance does not change from the initial stage even after object substance 8 is introduced.

As discussed above, surface plasmon sensor 1 of Embodiment 1 can measure the reaction between probe 6 and object substance 8 by measuring a change in the intensity of the second-order harmonic component of reflected light 10A with respect to the incident angle θ.

The lead perovskite-type material used to form dielectric film 5 is material expressed as a general formula of $ABO_3$. The A site includes at least Pb (lead), and one or more kinds of other elements may also be added to it. The B site contains one or more other kinds of elements. This material may also be a complex perovskite material having additional elements of different charge numbers, such as $A^{2+}(B^{2+}_{1/3}B^{5+}_{2/3})O_3$. Dielectric film 5 made of lead perovskite-type material having a high nonlinear optical effect provides surface plasmon sensor 1 with high efficiency.

According to Embodiment 1, the lead perovskite-type material of dielectric film 5 is PZT. The material may be material, such as lead titanate lanthanum (PLT), lead zirconate titanate lanthanum (PLZT), or lead titanate added with lanthanum and magnesium (PLMT), that has a high nonlinear optical effect.

Dielectric film 5 may be made of non-lead inorganic nonlinear optical material instead of the lead perovskite-type material. The non-lead inorganic nonlinear optical material is an inorganic material not containing Pb in any of the A site and B site, and has a high nonlinear optical effect.

The non-lead inorganic nonlinear optical material can make sensor 1 less harmful to the environment, and therefore, sensor 1 becomes readily disposable. It also eliminates the need for being concerned about a residue of Pb in a reagent during measurement, and makes the reagent readily disposable. Moreover, the absence of Pb can avoid cytotoxicity attributable to Pb as well as impediment of biomolecular reaction. Here, the non-lead inorganic nonlinear optical material can be any of borate group materials, such as crystal, potassium dihydrogen phosphate (KDP) and $LiB_3O_5$ (LBO), or $KTiOPO_4$ (KTP). In addition, the non-lead inorganic nonlinear optical material may also be one of ilmenite type materials, such as $LiTaO_3$ or $LiNbO_3$, tungsten-bronze type materials, such as $BaNaNbO_3$, or perovskite type materials, such as $K(Ta,Nb)O_3$, not containing Pb in the A site, and other materials, such as $Bi_3Ti_4O1_2$, having a layered perovskite structure. In any of the above-listed ilmenite type materials, tungsten-bronze type materials, perovskite type materials not containing Pb in the A site and other materials having a layered perovskite structure, any elements other than Pb may be added to the A and B sites, or any such elements may be added to the A and B sites having different charge numbers.

Dielectric film 5 can be made of polymer material. Dielectric film 5, upon being made of inorganic material like the lead perovskite type material or the non-lead inorganic nonlinear optical material, increases a resistance to heat. This allows surface plasmon resonance sensor 1 to have a superior characteristic and to be easily manufactured. Moreover, substrate 3 made of an inorganic material can improve strength of surface plasmon resonance sensor 1 more than substrate 3 made of an organic material, thereby allowing surface plasmon resonance sensor 1 to be easily handled. Dielectric film 5 made especially of any such material as the lead perovskite type material or the non-lead inorganic material having a nonlinear optical effect can cause a thermal expansion coefficient of dielectric film 5 to be close to that of substrate 3 of the inorganic material, thereby reducing warpage of them in the process of manufacturing. Substrate 3 can be made of light-transmittable glass of inorganic material that allows light to penetrate. The inorganic material, such as lead perovskite type material or non-lead inorganic nonlinear optical material, instead of an organic material, to form dielectric film 5 can reduce a moisture absorption effect of dielectric film 5, thereby provides surface plasmon resonance sensor 1 with high stability providing a small change in the frequency of the plasmon resonance.

Dielectric film 5 made of the lead perovskite type material or the non-lead inorganic nonlinear optical material can be formed by a method, such as a vacuum deposition method, a sputtering method, a sol-gel processing method, or a chemical vapor deposition (CVD) method. In particular, the sputtering method is useful to couple dielectric film 5 strongly with substrate 3 since dielectric film 5 is formed by vaporized molecules rushed from a target against substrate 3 at a high speed. Polymer made of organic substance cannot take the advantages mentioned above since it is not suitable to form dielectric film 5 by the sputtering method.

On the other hand, the CVD method is suitable to form uniform dielectric film 5 easily on a surface of large irregularities since a film formed by the CVD method can cover bumps easily and reliably.

In surface plasmon resonance sensor 1 according to Embodiment 1, substrate 3 has a flat plate shape so that first surface 4 and second surface 7 are parallel to each other. However, both of first surface 4 and second surface 7 may have asperities, that is, first surface 4 and second surface 7 may not necessarily be parallel to each other.

In the conventional surface plasmon resonance sensor, a change in the reflectivity is measured based on the phenomenon that incident light is absorbed and not reflected due to the surface plasmon resonance. However, since this change in the reflectivity is small, the conventional sensor is may not measure the surface plasmon resonance sensitively.

Surface plasmon resonance sensor 1 of Embodiment 1 has a high sensitivity since the amount of the change of the intensity of the light that changes due to the reaction between probe 6 and object substance 8 is large. In other words, sensor 1 employs second-order harmonic generation (SHG), one of the nonlinear optical effects, to measure the change of the reflected light based on the change of intensity of the second-order harmonic wave. Since the second-order harmonic wave of the incident light changes largely due to the surface plasmon resonance, the second-order harmonic wave can be detected easily with measuring device 10. The intensity of the second-order harmonic wave changes significantly when the condition of the surface plasmon resonance changes due to the reaction between probe 6 and object substance 8. As a result, surface plasmon resonance sensor 1 can sensitively detect that probe 6 and object substance 8 have reacted to each other.

In surface plasmon resonance sensor 1 according to Embodiment 1, measuring device 10 measures the change of the intensity of the second-order harmonic wave enhanced by the surface plasmon resonance generated on dielectric film 5 made of PZT having a high nonlinear optical effect. Since the change of the intensity of the second-order harmonic has a high peak, the shift of the peak can be detected sensitively by measuring the shift of the peak with respect to the incident angle $\theta$.

According to the Embodiment 1, surface plasmon resonance sensor 1 uses dielectric film 5 made of high nonlinear optical effect, which can efficiently enhance the second-order harmonic of the light even when the light has a small energy. Sensor 1 can measure the shift of the peak of the second-order harmonic highly sensitively with a small energy.

According to Embodiment 1, surface plasmon resonance sensor 1 measures the change of the intensity of the second-order harmonic with respect to incident angle $\theta$. Since the surface plasmon resonance also causes a change of the wavelength of the resonance, the change of the condition of the surface plasmon resonance which changes due to the reaction between object substance 8 and probe 6 can be detected by measuring the change in the intensity of the second-order harmonic with respect to the wavelength of incident light 9A.

According to the Embodiment 1, surface plasmon resonance sensor 1 uses the second-order harmonic generation (SHG), which is a secondary nonlinear optical effect as one of the nonlinear optical effects of dielectric film 5. Alternatively, surface plasmon resonance sensor 1 according to Embodiment 1 may employ other nonlinear optical effects of dielectric film 5, such as third-order nonlinear optical generation (THG) which is the third-order nonlinear optical effect, fourth-order harmonic generation which is the fourth nonlinear optical effect, and n-th-order harmonic generation which is the n-th nonlinear optical effect. Here, n is an integer larger than one. In other words, surface plasmon resonance sensor 1 according to Embodiment 1 may detect the reaction between object substance 8 and probe 6 by sensing the change of the condition of the plasmon resonance according to a shift of the peak or a change of frequency of the peak of any of the third-order harmonic component having frequency $3\omega$, the fourth-order harmonic component having frequency $7\omega$, and the n-th-order harmonic component having frequency $n\omega$ of the reflected light 10A corresponding to the incident light 9A of frequency $\omega$.

Surface plasmon resonance sensor 1 can detect the reaction between object substance 8 and probe 6 by sensing the change of the condition of the plasmon resonance enhanced by other nonlinear optical effect, such as an electro-optical (EO) effect which is the primary nonlinear optical effect which causes a change of the refractive index of dielectric film 5, an electro-optical Kerr effect which is the third-order nonlinear optical effect, and a parametric oscillation effect which changes incident light of a monochromatic wavelength into white radiation.

In surface plasmon resonance sensor 1 according to Embodiment 1, probe 6 is an antigen that is coupled specifically with an antibody, or object substance 8. Probe 6 may also be a DNA or RNA, or a functional molecule, such as protein and glucide, which is coupled specifically with object substance 8.

In surface plasmon resonance sensor 1 according to Embodiment 1, prism 2 radiates p-polarized light of incident light 9A to second surface 7 of the substrate under the condition of total reflection. Surface plasmon resonance sensor 1 does not necessarily include prism 2 if p-polarized light of incident light 9A can be radiated to second surface 7 of the substrate under the condition of total reflection. In sensor 1 does not include prism 2, substrate 3 may be placed on an optical waveguide, or substrate 3 may be a grating coupler waveguide having two layers having different indexes of refraction.

Exemplary Embodiment 2

Figure 3:
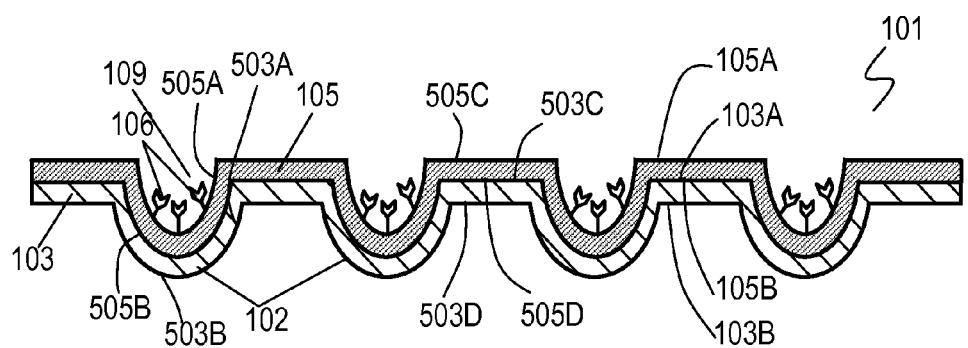
FIG. 3 is a sectional view of a localized plasmon resonance sensor according to Exemplary Embodiment 2 of the invention.
Figure 4:
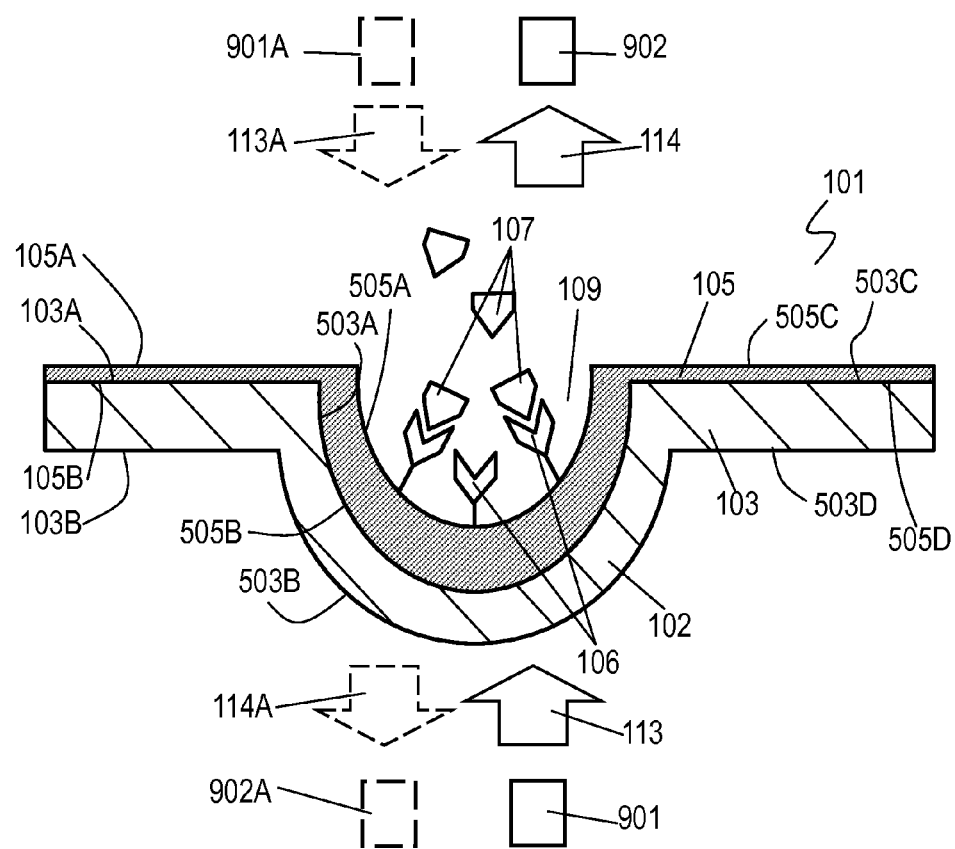
FIG. 4 is an enlarged sectional view of the localized plasmon resonance sensor according to Embodiment 2.

FIGS. 3 and 4 are a sectional view and an enlarged sectional view of localized plasmon resonance sensor 101 according to Exemplary Embodiment 2 of the present invention, respectively. Localized plasmon resonance sensor 101 includes substrate 103 having a plate shape, dielectric film 105 bonded to substrate 103, and probe 106 fixed to dielectric film 105. Substrate 103 has first surface 103A and second surface 103B opposite to first surface 103A. Dielectric film 105 is made of lead zirconate titanate (PZT). Dielectric film 105 has second surface 105B situated on first surface 103A of substrate 103, and first surface 105A opposite to second surface 105B. Probe 106 is fixed to first surface 105A of dielectric film 105. Dielectric film 105 has plural concave portions 109 provided in first surface 105A thereof. Second surface 103B of substrate 103 has plural convex portions 102 at positions opposite to plural concave portions 109, respectively. First surface 105A of dielectric film 105 has concave surfaces 505A facing concave portion 109, respectively. Second surface 105B of dielectric film 105 has convex surfaces 505B opposite to concave surfaces 505A, respectively. First surface 103A of substrate 103 has concave surfaces 503A formed along convex surfaces 505B. Second surface 103B of substrate 103 has convex surfaces 503B opposite to concave surfaces 503A, respectively. Convex surfaces 503B constitute convex portions 102. Probes 106 are fixed to concave surfaces 505A in first surface 105A of dielectric film 105. Probes 106 are functional molecules having a function reacting specifically with and coupled specifically with object substance 107. In localized plasmon resonance sensor 101 according to Embodiment 2, object substance 107 is a specific antibody, and probe 106 is a functional molecule that has the function coupled specifically with the antibody.

In convex portions 102, first surfaces 103A (concave surfaces 503A) of substrate 103 and second surfaces (convex surfaces 505B) have curved surfaces that protrude in the same direction. Concave portions 109 facing dielectric film 105 are located opposite to convex portions 102. Probes 106 are fixed to concave surfaces 505A in first surface 105A of dielectric film 105 that constitute inner surfaces of concave portions 109. Plural convex portions 102 preferably have the same shape and arranged at constant intervals.

According to Embodiment 2, substrate 103 has a thickness ranging from about 5 nm to 50 nm, and dielectric film 105 has a thickness ranging from about several nanometers to 10 nm.

Dielectric film 105 is preferably made of material which produces an intensive nonlinear polarization, and which is easily processed to have a micro shape. According to Embodiment 2, dielectric film 105 is made of PZT, however, may be made of material selected from the group consisting of lead perovskite-type materials, such as lead titanate lanthanum (PLT), lead zirconate titanate lanthanum (PLZT), and lead titanate (PLMT) as well as non-lead inorganic nonlinear optical materials.

Substrate 103 is made of material, such as platinum, gold, silver, or copper, can generate plasmon on a surface thereof. In this Embodiment 2, substrate 103 is formed of platinum. Platinum has a lattice constant close to that of dielectric film 105 made of PZT or PLMT, and allows dielectric film 105 to be uniform over microscopic concave surfaces 503A, which can improve crystallinity of dielectric film 105, and further increase the nonlinear optical effect of dielectric film 105.

A method of manufacturing localized plasmon resonance sensor 101 according to Embodiment 2 will be described below. FIGS. 5 to 8A are sectional views of localized plasmon resonance sensor 101 for illustrating the method of manufacturing sensor 101.

Figure 5:
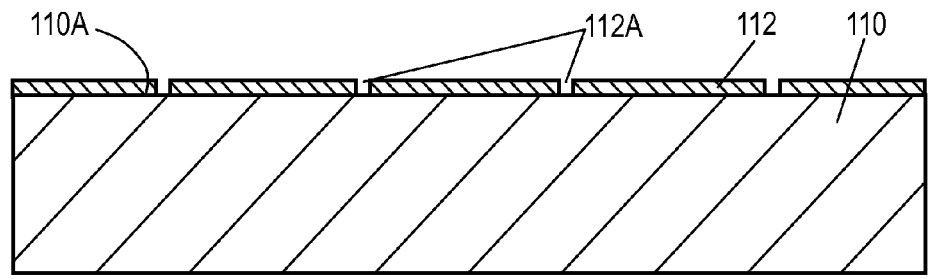
FIG. 5 is a sectional view of the localized plasmon resonance sensor according to Embodiment 2 for illustrating a method of manufacturing the sensor.

First, base 110 shown in FIG. 5 is prepared. According to Embodiment 2, a mono-crystal silicon substrate suitable for micro-fabrication is prepared as base 110.

Figure 6:
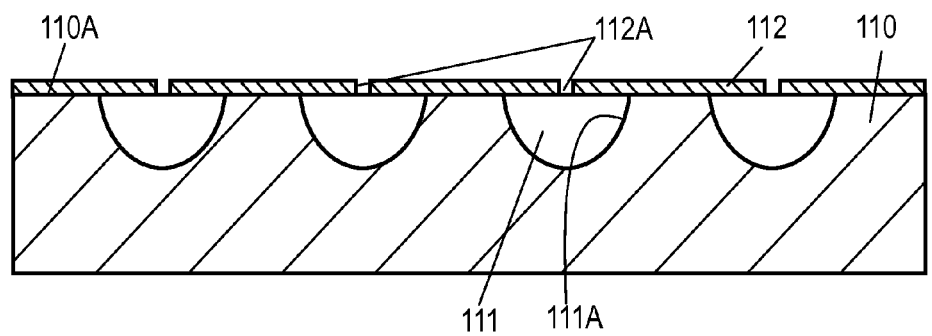
FIG. 6 is a sectional view of the localized plasmon resonance sensor according to Embodiment 2 for illustrating the method of manufacturing the sensor.

Next, mask 112 having mask holes 112A formed therein is placed on surface 110A of base 110. Then, pits 111 shown in FIG. 6 are formed in surface 110A by dry etching base 110 through mask holes 112A with an etching gas. The etching gas used here may be $SF_6$, $CF_4$, $NF_3$, $XeF_2$, or mixture of these gases. Any of these gases facilitates etching of the silicon substrate not only in its depth direction but also along surface 110A, or a horizontal direction perpendicular to the depth direction, thereby easily forming pits 111 having a semi-spherical bowl-like shape in base 110.

The above etching gases according to Embodiment 2 are mixed with a carrier gas, such as N2, Ar, He, or $H_2$. The carrier gas facilitates the above etching diffusing uniformly, and makes inner surfaces 111A of pits 111 smooth. Smooth inner surfaces 111A of pits 111 allow pits 111 to have a simple shape while avoiding complicated shape, so as to make pits 111 having substantially the same shape. A mono-crystal silicon substrate of (100) plane orientation is especially suitable to form pits 111 having the semi-spherical shape among various mono-crystal silicon substrates available for base 110. A mono-crystal silicon substrate of (110) plane orientation is used for base 110 when pits 111 of a half elliptic semi-spherical shape are desired. A mono-crystal silicon substrate of (111) plane orientation may not suitable to form pits 111 in the depth direction or the horizontal direction since etching does not progress effectively in these directions, and pits 111 cannot be formed evenly.

In the dry etching process according to Embodiment 2, the interiors of pits 111 are charged with the etching gas by injecting the gas from above mask 112 through mask holes 112A. The injected gas remains in pits 111 for a predetermined duration, and then, the etching gas is sucked and retrieved. This process is repeated plural times to allow the etching gas to diffuse uniformly, thereby making inner surfaces 111A of pits 111 smooth.

Figure 7:
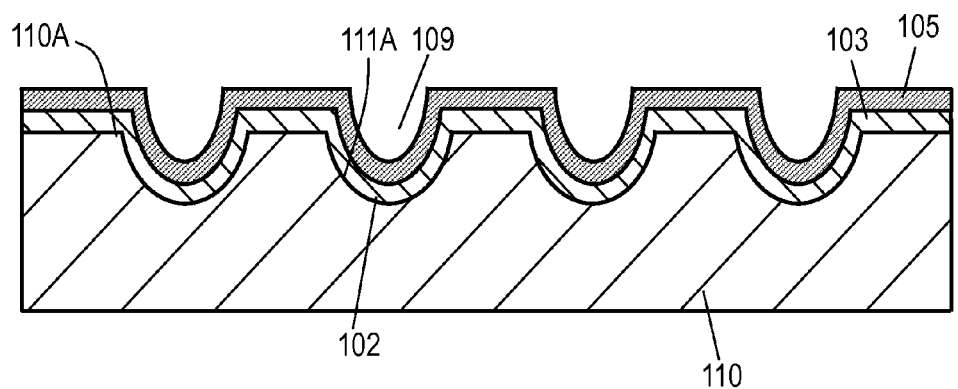
FIG. 7 is a sectional view of the localized plasmon resonance sensor according to Embodiment 2 for illustrating the method of manufacturing the sensor.

Then, mask 112 is removed, and platinum is sputtered entirely on surface 110A of base 110 to form a film that constitutes substrate 103, as shown in FIG. 7. Substrate 103 is formed to have a thin and substantially uniform thickness so as to cover surface 110A of base 110 while having an undulating shape along inner surfaces 111A of pits 111 in base 110.

After that, PZT is sputtered on first surface 103A of substrate 103 to form dielectric film 105 of the PZT. Dielectric film 105 is also undulated along pits 111 of base 110 to cover surface 103A of substrate 103.

Although substrate 103 can be formed by a deposition method, substrate 103 formed by the sputtering method can improve its crystallinity, which in turn improves crystallinity of dielectric film 105 deposited thereon, thereby increasing the nonlinear polarization of dielectric film 105. While dielectric film 105 itself can be formed by any of the deposition and sol-gel methods, the sputtering method can improve its crystallinity and increase the nonlinear polarization.

Figure 8A:
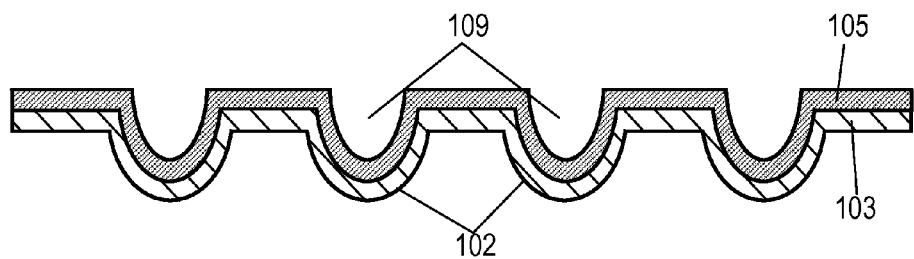
FIG. 8A is a sectional view of the localized plasmon resonance sensor according to Embodiment 2 for illustrating the method of manufacturing the sensor.

Then, according to Embodiment 2, base 110 is removed by an etching process, such as dry etching using $XeF_2$ gas or wet etching, as shown in FIG. 8A. Probes 106 are fixed to concave surfaces 505A, or the inner surfaces of concave portions 109 of first surface 105A of dielectric film 105, as shown in FIG. 3 and FIG. 4, thus providing localized plasmon resonance sensor 101.

Figure 8B:
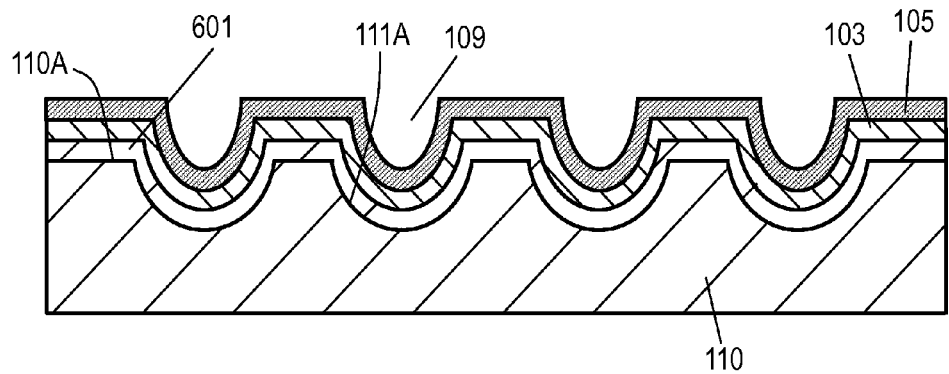
FIG. 8B is a sectional view of the localized plasmon resonance sensor according to Embodiment 2 for illustrating another method of manufacturing the sensor.

FIG. 8B is a sectional view of localized plasmon resonance sensor 101 for illustrating another method of manufacturing the sensor 101. In FIG. 8B, components identical to those of the sensor shown in FIG. 7 are denoted by the same reference numerals. As shown in FIG. 8B, foundation layer 601 made of titanium having a thickness of about ⅕ to ¹⁄₁₀ of substrate 103 is preferably formed before sputtering platinum to form substrate 103 on surface 110A of base 110. Platinum is then sputtered on foundation layer 601 to form substrate 103. Foundation layer 601 allows the platinum to deposit uniformly to obtain substrate 103 having a uniform thickness.

Referring to FIG. 4, a method of measuring reaction between probes 106 and object substance 107 in localized plasmon resonance sensor 101 according to Embodiment 2 will be described below. Light projector 901 radiates incident light 113 to localized plasmon resonance sensor 101. Localized plasmon resonance sensor 101 generates light 114 in response to incident light 113. In localized plasmon resonance sensor 101, light 114 contains a component generated by the nonlinear optical effect of dielectric film 105 from incident light 113. According to Embodiment 2, the nonlinear optical effect is a secondary nonlinear optical effect, and the component is a second-order harmonic (SH) wave. Measuring device 902 measures a change in intensity of the second-order harmonic component of light 114 corresponding to a wavelength of incident light 113 to detect the reaction. The second-order harmonic component is a component having a frequency $2\omega$, which is twice the frequency $\omega$ of incident light 113.

When incident light 113 having a predetermined frequency is radiated to convex surface 503B of convex portion 102, incident light 113 excites free electrons in convex portion 102 to provide the electrons with resonance vibration with a frequency of electric field of incident light 113, hence producing localized plasmon resonance. Simultaneously, the localized plasmon resonance significantly increases an intensity of the electric field around convex surface 505B of dielectric film 105 contacting concave surface 503A of substrate 103 opposite to convex portion 102, thereby generating light 114 containing a second-order harmonic (SH) component having the frequency 2ω due to the nonlinear optical effect of dielectric film 105. Light 114 can be detected with measuring device 902 from first surface 105A of dielectric film 105. Light 114A is also generated from second surface 105B of dielectric film 105 due to the nonlinear optical effect from incident light 113, and light 114A can be detected with measuring device 902A. In other words, lights 114 and 114A are radiated from first surface 105A of dielectric film 105 and second surface 105B of dielectric film 105, i.e., second surface 103B of substrate 103, respectively, as shown in FIG. 4.

Figure 9:
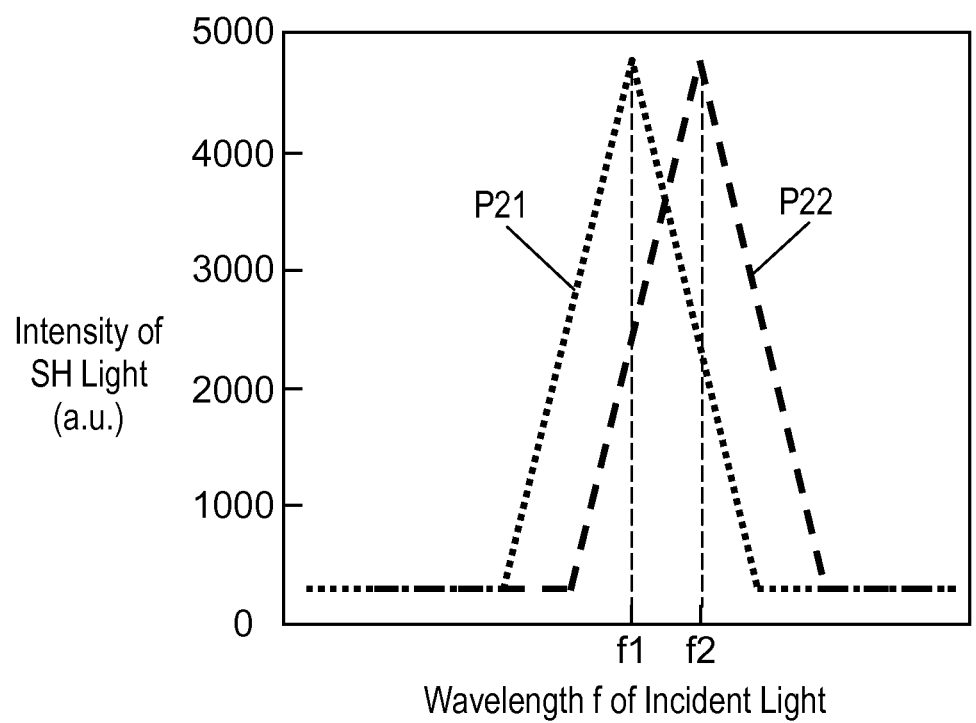
FIG. 9 shows a characteristic of the localized plasmon resonance sensor according to Embodiment 2.

FIG. 9 shows a characteristic of intensity of the second-order harmonic (SH) component of light 114 generated from localized plasmon resonance sensor 101. In FIG. 9, the vertical axis represents the intensity of the second-order harmonic (SH) component of light 114, and the horizontal axis represents the wavelength of incident light 113. Profile P21 shows an intensity of the second-order harmonic component of light 114 at an initial stage before probe 106 react to object substance 107. At the initial stage, when incident light 113, upon having wavelength f1, causes localized plasmon resonance at convex portion 102, and increases the electric field on second surface 105B.

Here, the nonlinear polarization of dielectric film 105 increases in proportion to the second power of the intensity of the electric field of incident light 113, and the intensity of the second-order harmonic wave increases in proportion to the fourth power of the intensity of the electric field of incident light 113. The second-order harmonic wave can therefore be detected sensitively. The sensitivity of detecting a change in the condition of plasmon resonance can be improved by sensing light of a higher-order term than light of a first-order term in the light generated by the nonlinear optical effect. In localized plasmon resonance sensor 101 of Embodiment 2, the intensity of the second-order harmonic wave becomes very high since it is provided with dielectric film 105 featuring a high nonlinear polarization capability. According to Embodiment 2, the second-order harmonic wave is enhanced to about 1000 times due to the localized plasmon resonance, and it exhibits a highest peak at the resonant frequency having wavelength f1, as shown in FIG. 9.

Next, object substance 107 is introduced to probe 106 to cause a reaction between probe 106 and object substance 107. A dielectric constant and a refractive index of the surface of dielectric film 105 change when object substance 107, or an antibody exhibits an antigen-antibody reaction with probe 6 to be coupled with probe 6, or an antigen. Since a wave number of the localized plasmon developed on convex portion 102 is dependent upon a dielectric constant near convex surface 505B in concave portion 109 and concave surface 505A as well as a refractive index of a medium contacting convex portion 102, the resonance condition of developing the plasmon resonance changes due to the coupling of object substance 107 with probe 106.

In localized plasmon resonance sensor 101 of Embodiment 2, an intensity of the second-order harmonic component of light 114 exhibits the highest peak when incident light 113 has wavelength f2, and the resonant frequency shifts due to the coupling between probe 106 and object substance 107, after the introducing of object substance 107. It is estimated that introduced object substance 107 does not react with probe 106 if the resonant frequency does not shift from that of the initial stage even after the introducing of object substance 107.

According to Embodiment 2, as discussed above, localized plasmon resonance sensor 101 can measure the reaction between probe 106 and object substance 107 by monitoring a change in the intensity of the second-order harmonic component corresponding to the wavelength or frequency of incident light 113.

Localized plasmon resonance sensor 101 of Embodiment 2 has a high sensitivity because of its advantage of increasing a degree of change in the intensity of the light due to the reaction between probe 106 and object substance 107.

The electric field is increased by the localized plasmon resonance to enhance the nonlinear optical effect of dielectric film 105. Localized plasmon resonance sensor 101 of Embodiment 2 includes dielectric film 105 having a higher nonlinear polarization, accordingly exerts even higher nonlinear optical effect, thereby enhancing the intensity of the second-order harmonic wave, which is a nonlinear optical effect. As a result, the intensity of the second-order harmonic component of light 114 changes with a large peak value in response to the wavelength or the frequency of incident light 113. Localized plasmon resonance sensor 101 can thus detect the reaction between probe 106 and object substance 107 sensitively by measuring a shift of this peak point before and after the reaction. In other words, localized plasmon resonance sensor 101 has a high sensitivity since the intensity of the second-order harmonic component of incident light 113 changes significantly in light 114 with a change in the resonance condition of the plasmon resonance due to the reaction between probe 106 and object substance 107.

In addition, since localized plasmon resonance sensor 101 of Embodiment 2 can exert a high nonlinear optical effect, it can efficiently enhance the second-order harmonic of the light even when the light has a weak energy, and therefore, sensor 101 can measure the reaction between probe 106 and object substance 107 highly sensitively with a reduced energy.

In localized plasmon resonance sensor 101 according to Embodiment 2, base 110 made of a mono-crystal silicon substrate is prepared by a semiconductor fabrication process, such as thin film processing or photolithographic technique, and substrate 103 and dielectric film 105 are then deposited by a thin film processing. These processes facilitate the fabrication of microscopic convex portions 102 and concave portions 109 at once precisely, accordingly allowing tiny and high-precision localized plasmon resonance sensors 101 to be manufactured efficiently.

According to Embodiment 2, localized plasmon resonance sensor 101 utilizes the second-order harmonic generation (SHG), which is a secondary nonlinear optical effect as one of the nonlinear optical effects of dielectric film 105. However, localized plasmon resonance sensor 101 of Embodiment 2 may utilize any other nonlinear optical effects of dielectric film 105, such as a third-order harmonic generation (THG) which is the third nonlinear optical effect, fourth-order harmonic generation which is the fourth nonlinear optical effect, and n-th-order harmonic generation which is the n-th nonlinear optical effect (where n is an integer larger than one). In other words, localized plasmon resonance sensor 101 of Embodiment 2 may detect the reaction between object substance 107 and probe 106 by sensing the change in the condition of the plasmon resonance according to a shift of the peak or a change in frequency of the peak of any of the third-order harmonic component having frequency 3ω, the fourth-order harmonic component having frequency 4ω, and the n-th-order harmonic component having frequency nω within the reflected light 10A corresponding to the incident light 9A having frequency ω, Localized plasmon resonance sensor 101 can detect the reaction between object substance 107 and probe 106 by sensing the change in the condition of the plasmon resonance enhanced by any other nonlinear optical effects, such as an electro-optical (EO) effect which is the primary nonlinear optical effect of causing a change in the refractive index of dielectric film 105, an electro-optical Kerr effect which is the third nonlinear optical effect, and a parametric oscillation effect which turns incident light of a monochromatic wavelength into an output of white radiation.

In localized plasmon resonance sensor 101 of Embodiment 2, probe 106 is an antigen that is coupled specifically with an antibody, or object substance 107. Probe 106 may also be a DNA or RNA, or a functional molecule, such as protein or glucide, which is coupled specifically with object substance 107.

Figure 10A:
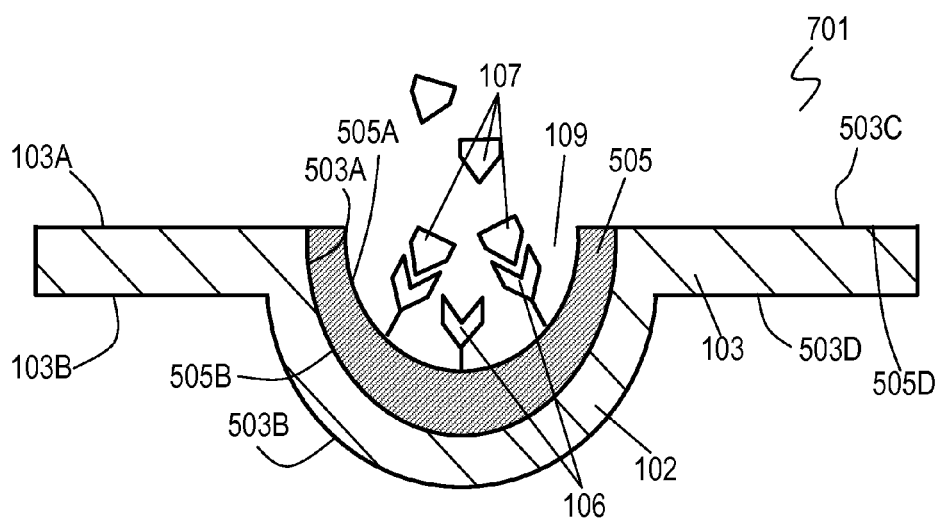
FIG. 10A is a sectional view of another localized plasmon resonance sensor according to Embodiment 2.

FIG. 10A is a sectional view of another localized plasmon resonance sensors 701 according to Embodiment 2. In FIG. 10A, components identical to those of localized plasmon resonance sensor 101 shown in FIGS. 3 and 4 are denoted by the same reference numerals. Localized plasmon resonance sensor 701 shown in FIG. 10A includes dielectric film 505 instead of dielectric film 105 of localized plasmon resonance sensor 101 shown in FIGS. 3 and 4. Dielectric film 505 is made of material similar to that of dielectric film 105, and has a thickness similar to that of dielectric film 105.

As shown in FIGS. 4 and 10A, first surface 103A of substrate 103 includes plural concave surfaces 503A and flat portion 503C having a flat surface provided around the concave surfaces 503A and connected with concave surfaces 503A. Second surface 103B of substrate 103 has plural convex surfaces 503B and flat portion 503D having a flat surface provided around convex surfaces 503B and connected with convex surfaces 503B. Flat portion 503D is located opposite to flat portion 503C. In localized plasmon resonance sensor 101 shown in FIGS. 3 and 4, dielectric film 105 is disposed on all of concave surfaces 503A and flat portion 503C of first surface 103A of substrate 103. In localized plasmon resonance sensor 701 shown in FIG. 10A, dielectric film 505 is disposed only on concave surfaces 503A of first surface 103A of substrate 103, but it is not disposed on flat portion 503C. In other words, flat portion 503C is exposed from dielectric film 505. Dielectric film 505 has convex surface 505B disposed on concave surface 503A of substrate 103, and concave surface 505A opposite to convex surface 505B, similarly to dielectric film 105 shown in FIGS. 3 and 4. Concave surface 505A of dielectric film 505 faces concave portion 109 having plural probes 106 fixed thereto. Localized plasmon resonance sensor 701 shown in FIG. 10A has similar effects as those of localized plasmon resonance sensor 101 shown in FIGS. 3 and 4.

Figure 10B:
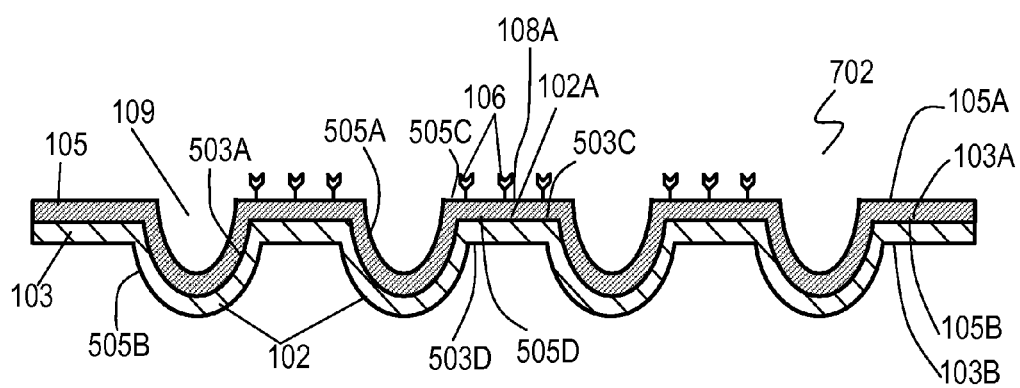
FIG. 10B is a sectional view of still another localized plasmon resonance sensor according to Embodiment 2.

FIG. 10B is a sectional view of still another localized plasmon resonance sensors 702 according to Embodiment 2. In FIG. 10B, components identical to those of localized plasmon resonance sensor 101 shown in FIG. 3 and FIG. 4 are denoted by the same reference numerals.

As shown in FIGS. 4 and 10B, second surface 105B of dielectric film 105 has flat portion 505D situated on flat portion 503C of first surface 103A of substrate 103. Flat portion 505D is connected with convex surfaces 505B. First surface 105A of dielectric film 105 has flat portion 505C having a flat surface opposite to flat portion 505D of second surface 105B. Flat portion 505C is connected with concave surfaces 505A. In localized plasmon resonance sensor 702 shown in FIG. 10B, probes 106 are not provided on concave surfaces 505A facing concave portions 109, but are provided on flat portion 505C of dielectric film 105. Concave surfaces 503A of substrate 103 and flat portion 503C connected with concave surfaces 503A constitute convex surfaces 108A that includes convex portions 102A protruding in a direction opposite to convex portions 102. In other words, localized plasmon resonance sensor 702 includes dielectric film 105 provided on convex surfaces 108A of convex portions 102A. Flat portions 505D of second surface 105B of dielectric film 105 are situated in convex surfaces 108A of convex portions 102A, and probes 106 are fixed to flat portions 505C of first surface 105A opposite to flat portions 505D. In localized plasmon resonance sensor 702, localized plasmon resonance can be generated near surfaces 108A by setting conditions, such as a shape and size of convex portions 102A and a refractive index of the surfaces.

Figure 10C:
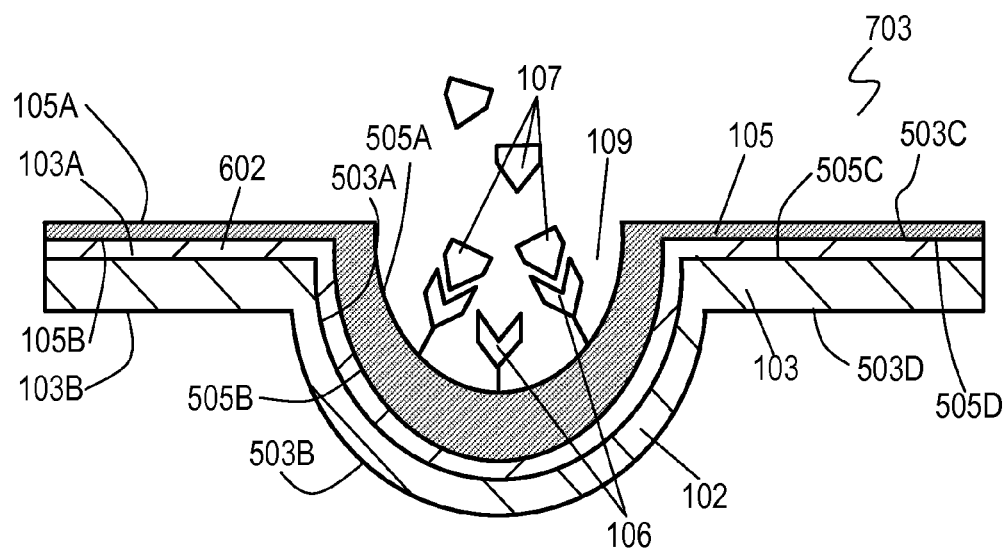
FIG. 10C is a sectional view of a further localized plasmon resonance sensor according to Embodiment 2.

FIG. 10C is a sectional view of further localized plasmon resonance sensor 703 according to Embodiment 2. In FIG. 10C, components identical to those of localized plasmon resonance sensor 101 shown in FIGS. 3 to 8A are denoted by the same reference numerals. Localized plasmon resonance sensor 703 shown in FIG. 10C further include oxide dielectric layer 602 disposed between substrate 103 and dielectric film 105. Oxide dielectric layer 602 is made of oxide dielectric material, such as PLMT containing Pb and Ti. Oxide dielectric layer 602 can improve crystalline orientation of dielectric film 105, so as to provide accurate localized plasmon resonance sensor 702.

Although convex portion 102 according to Embodiment 2 has a semi-spherical shape, convex portion 102 may have a half elliptic semi-spherical shape when a mono-crystal silicon substrate of (110) plane orientation is used for base 110, as described above. Pits 111 can be provided in base 110 to have a pyramid shape, a circular cylindrical shape, or a prismatic shape by using an anisotropic dry etching to process base 110. Convex portions 102 can have a shape corresponding to any of these shapes by forming substrate 103 on pits 111. In addition, pits 111 can have a cross section having a U-shape. Pits 111 may have inner surfaces 111A formed into a step-like shape by controlling convection of the etching gas. Accordingly, convex portions 102 can have a shape corresponding to the shape of pits 111. In Embodiment 2, a mono-crystal silicon substrate of (100) plane orientation or (110) plane orientation may preferably be used as a material of base 110, which facilitate fabrication of pits 111 uniformly. Pits 111 can be formed relatively uniformly even when a polycrystalline silicon substrate or an amorphous silicon substrate is used for base 110. The material of base 110 is not necessarily just a silicon substrate, but may be any light-transmittable material, such as glass substrate quartz substrate. Pits 111 can be formed accurately in base 110 made of glass substrate or quartz substrate with HF gas as the etching gas.

Figure 10D:
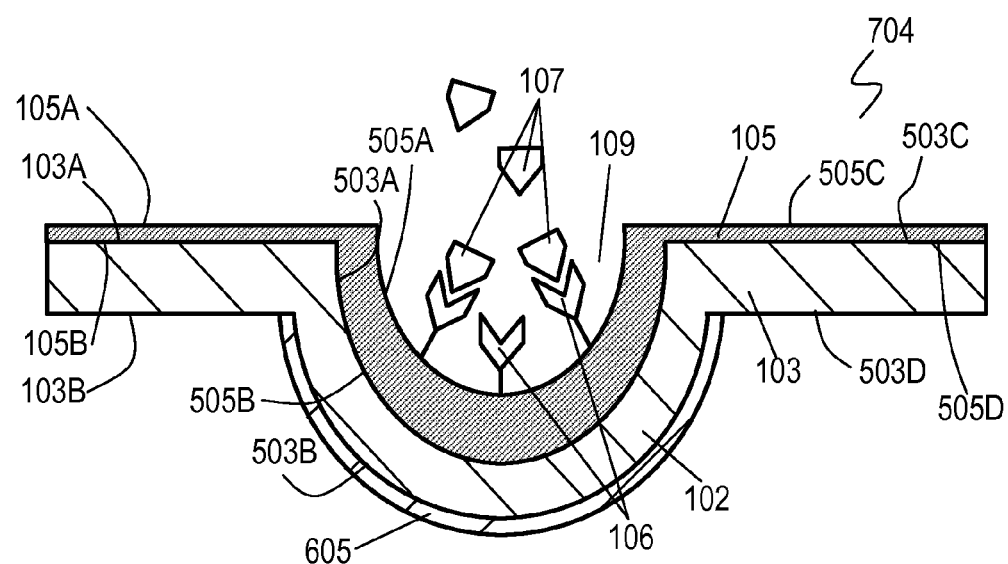
FIG. 10D is a sectional view of a further localized plasmon resonance sensor according to Embodiment 2.

FIG. 10D is a sectional view of further localized plasmon resonance sensors 704 according to Embodiment 2. In FIG. 10D, components identical to those of localized plasmon resonance sensor 101 shown in FIGS. 3 and 4 are denoted by the same reference numerals. Localized plasmon resonance sensor 704 shown in FIG. 10D further includes dielectric film 605 disposed on convex surface 503B of convex portion 102 in second surface 103B of substrate 103. Localized plasmon resonance sensor 704 has similar advantages as those of localized plasmon resonance sensor 101 shown in FIGS. 3 and 4.

As shown in FIG. 4, light projector 901 radiates light 113 to second surface 103B of substrate 103, and an antigen-antibody reaction between object substance 107 and probe 106, or an antigen and an antibody, is detected by sensing, with measuring device 902, light 114 radiated from dielectric film 105 provided on first surface 103A of substrate 103. This reaction may be detected with measuring device 902A and measuring a harmonic component of incident light 113, such as a second-order harmonic component of light 114A generated by the nonlinear optical effect and radiated from first surface 103B of substrate 103, as shown in FIG. 4. Measuring device 902A detecting light 114A radiated from second surface 103B of substrate 103 exposed from with dielectric film 105 can prevent the light from being attenuated by dielectric film 105, probes 106, and object substances 107, thus providing sensor 101 sensitively.

In localized plasmon resonance sensors 101 and 701 to 706 according to Embodiment 2, probes 106 are fixed not entirely to first surface 105A of dielectric film 105. This structure can reduce the density of probes 106 that attenuate the light, thereby improving the sensitivity of these sensors.

Figure 11:
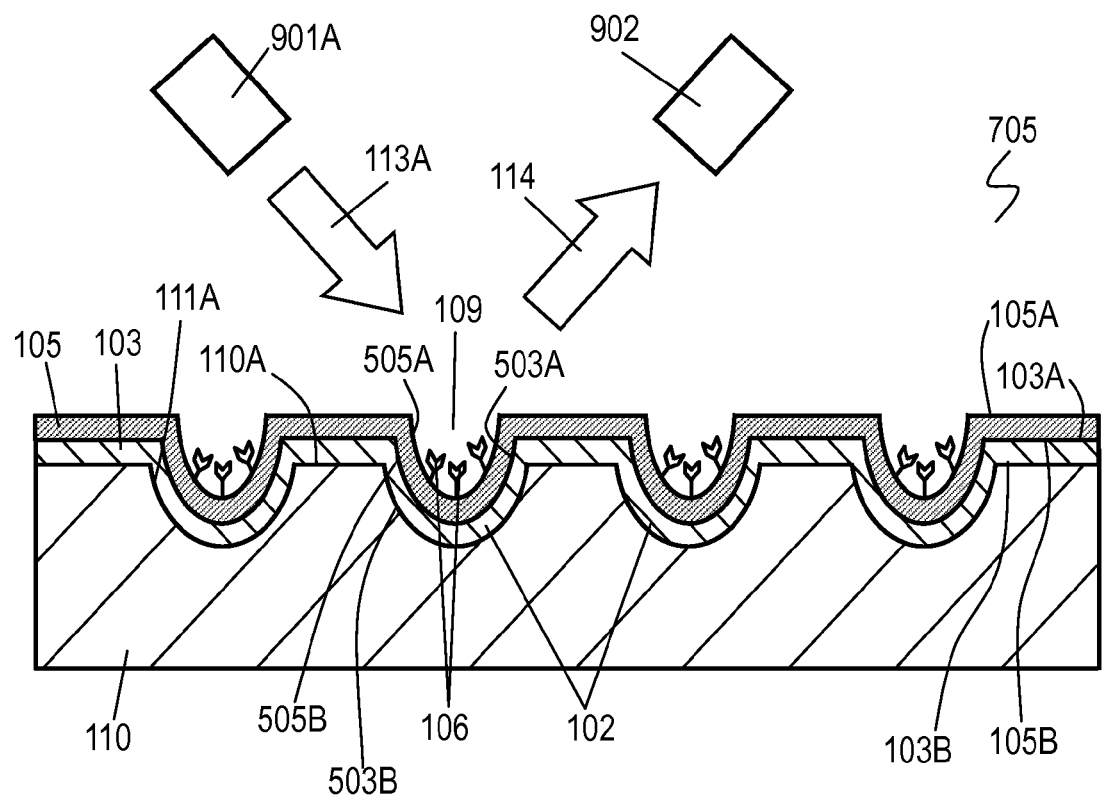
FIG. 11 is a sectional view of a further localized plasmon resonance sensor according to Embodiment 2.

FIG. 11 is a sectional view of further localized plasmon resonance sensors 705 according to Embodiment 2. In FIG. 11, components identical to those of localized plasmon resonance sensor 101 shown in FIGS. 3 to 8A are denoted by the same reference numerals. Localized plasmon resonance sensor 705 shown in FIG. 11 further includes base 110 made of mono-crystal silicon substrate similarly to the sensor shown in FIG. 7, in addition to localized plasmon resonance sensor 101 shown in FIG. 3. That is, base 110 shown in FIG. 7 remains without being removed, and probes 106 are fixed to concave surfaces 505A of first surface 105A, or inner surfaces 109A of concave portions 109 provided in dielectric film 105.

Since base 110 made of silicon allows visible light to pass therethrough, light projector 901A radiates incident light 113A toward concave portions 109 to generate localized plasmon resonance, and measuring device 902 measures light 114 reflected from base 110. More specifically, measuring device 902 measures a change in intensity of a component of light 114 generated by the nonlinear optical effect in response to incident light 113, a higher-order harmonic of incident light 113 for instance, similarly to localized plasmon resonance sensor 101 shown in FIG. 4. Accordingly, localized plasmon resonance sensor 705 can detect a reaction between object substance 107 and probe 106 sensitively similarly to localized plasmon resonance sensor 101.

If base 110 is made of a light-transmittable glass substrate, the incident light can travel through base 110 to irradiate substrate 103, and allows localized plasmon resonance sensor 705 to measure the light generated by the nonlinear optical effect in response to the incident light.

Exemplary Embodiment 3

Figure 12:
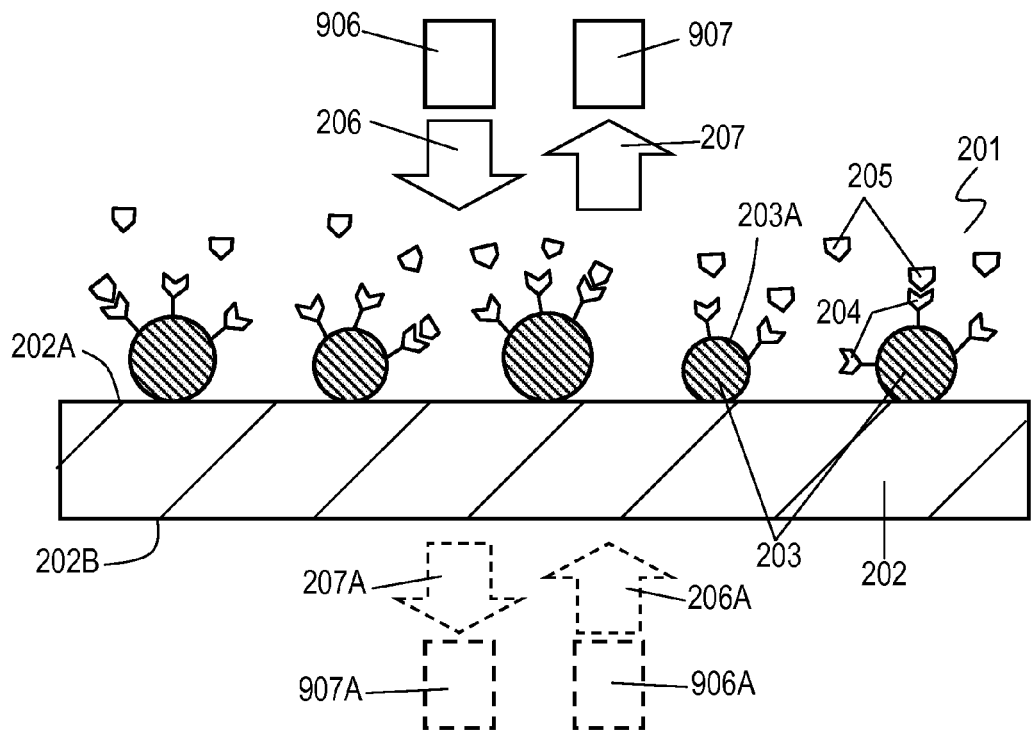
FIG. 12 is a sectional view of a localized plasmon resonance sensor according to Exemplary Embodiment 3 of the invention.

FIG. 12 is a sectional view of localized plasmon resonance sensor 201 according to Exemplary Embodiment 3. In FIG. 12, localized plasmon resonance sensor 201 of Embodiment 3 includes base 202, metal particles 203 disposed on surface 202A of base 202, and probes 204 disposed on surfaces 203A of metal particles 203. Base 202 has surface 202B opposite to surface 202A. Each of probes 204 specifically reacts to and is coupled with object substance 205. According to Embodiment 3, object substance 205 is a specific antibody, and probe 204 is an antigen that performs an antigen-antibody reaction and is coupled with the antibody.

Metal particles 203 are made of metal, such as gold or silver. A metal film is formed on surface 202A of base 202 by using the metal. Then, metal particles 203 are formed by applying heat to the metal film and granulate the metal. Since this simple process can form metal particles 203, localized plasmon resonance sensor 201 can be manufactured efficiently.

Light projector 906 radiates incident light 206 to surface 202A of base 202, as shown in FIG. 12. Measuring device 907 detects a change in intensity of light 207 radiated from surface 202A of base 202. Resonance conditions under which localized plasmon generated at interfaces between probes 204 and metal particles 203 resonate with incident light 206 changes before and after reaction of probes 204 to object substances 205. Localized plasmon resonance sensor 201 can detect the reaction of probes 204 to object substances 205 by monitoring the change in the intensity of detected light 207.

Base 202 may be made of light-transmittable material, such as glass, allowing light to pass therethrough. In this case, light projector 906A radiates incident light 206A to surface 202B of base 202 instead of incident light 206. In addition, measuring device 907A detects a change in intensity of light 207A reflected (radiated) from surface 202B of base 202 instead of light 207. The reaction of probes 204 to object substances 205 can be detected based on the detected change of the intensity. This structure of radiating incident light 206A to surface 202B of base 202 and detecting the intensity of light 207A radiated from surface 202B can prevent the light from being attenuated by probes 204 and object substances 205, hence providing localized plasmon resonance sensor 201 sensitively.

Figure 13A:
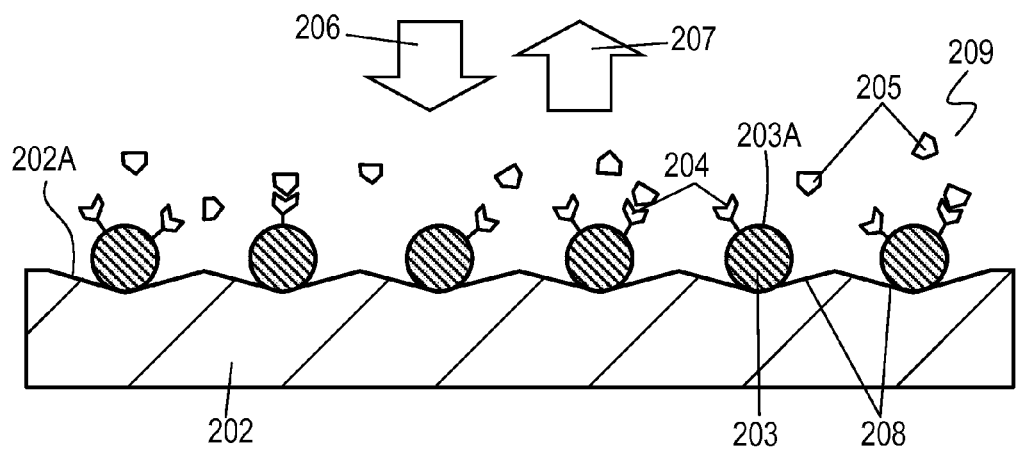
FIG. 13A is a sectional view of another localized plasmon resonance sensors according to Embodiment 3.

FIG. 13A is a sectional view of another localized plasmon resonance sensors 209 according to Embodiment 3. Localized plasmon resonance sensor 209 includes base 202. Surface 202A of base 202 has a cyclic undulating shape including concave portions 208, identical partial shapes arranged repetitively. More specifically, plural concave portions 208 arranged periodically at regular intervals in surface 202A of base 202. After a metal film including a thin layer made of the above metal is formed on surface 202A, the metal film is heated while surface 202A is directed upward to melt the metal film and cohere the metal. This process can form metal particles 203 having shapes substantially identical to each other located on concave portions 208. In other words, metal particles 203 having the identical shapes are arranged regularly at constant intervals on surface 202A of base 202. This configuration can reduce variations in the resonance frequency for generating a plasmon resonance in localized plasmon resonance sensor 209.

In localized plasmon resonance sensor 209 shown in FIG. 13A, surface 202A of base 202 has the cyclic undulating shape including concave portions 208 arranged repetitively, but may have a cyclic shape including other shapes arranged repetitively.

Figure 13B:
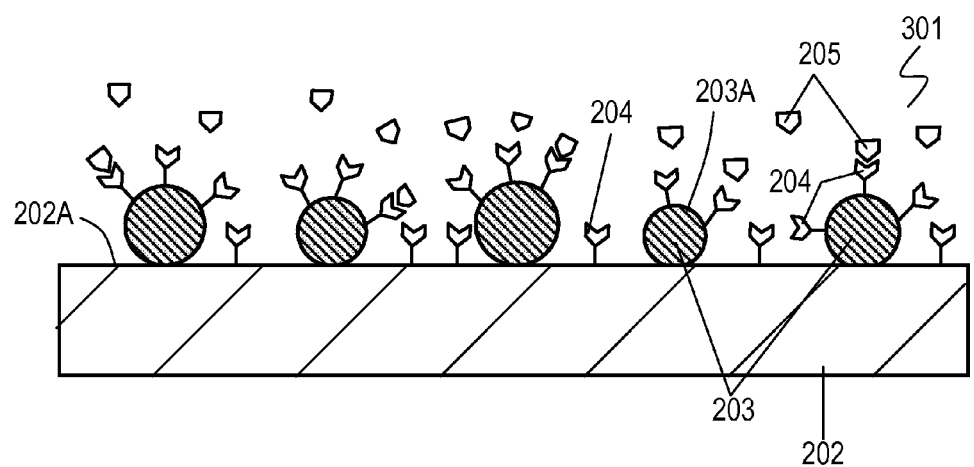
FIG. 13B is a sectional view of still another localized plasmon resonance sensor according to Embodiment 3.

FIG. 13B is a sectional view of another localized plasmon resonance sensors 301 according to Embodiment 3. In FIG. 13B, components identical to those of localized plasmon resonance sensor 201 shown in FIG. 12 are denoted by the same reference numerals. Localized plasmon resonance sensor 301 shown in FIG. 13B includes probes 204 disposed on surface 202A of base 202 in addition to the probes on metal particles 203, providing the same effects. Since this structure can be formed without a complex manufacturing process, it improves production efficiency of localized plasmon resonance sensor 301.

Figure 13C:
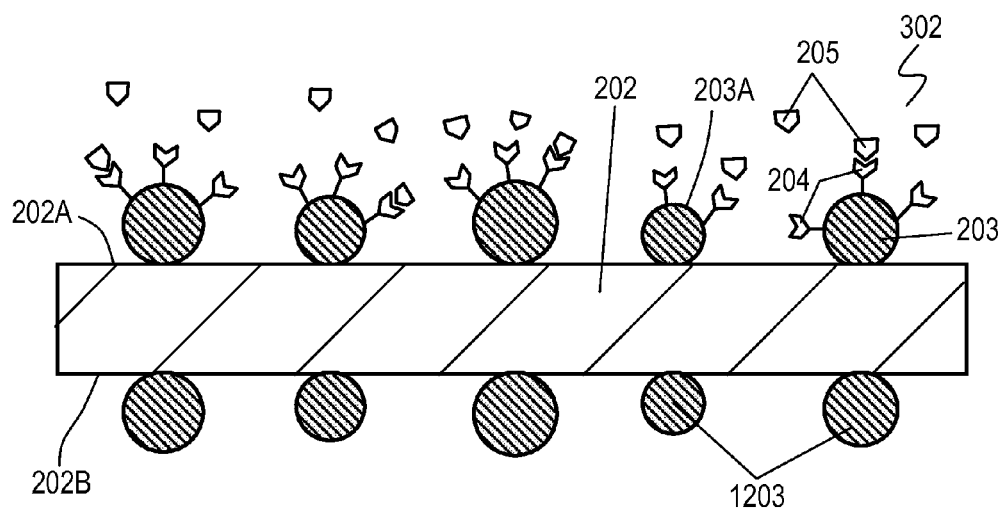
FIG. 13C is a sectional view of a further localized plasmon resonance sensor according to Embodiment 3.

FIG. 13C is a sectional view of still another localized plasmon resonance sensors 302 according to Embodiment 3. In FIG. 13C, components identical to those of localized plasmon resonance sensor 201 shown in FIG. 12 are denoted by the same reference numerals. Localized plasmon resonance sensor 302 shown in FIG. 13C includes not only metal particles 203 on surface 202A, but also similar metal particles 1203 disposed on surface 202B of base 202. This structure provides localized plasmon resonance sensor 302 has a higher sensitivity than localized plasmon resonance sensor 201.

A method of manufacturing localized plasmon resonance sensor 209 shown in FIG. 13A will be described below. FIGS. 14A to 14D are sectional views of localized plasmon resonance sensor 209 for illustrating the method of manufacturing the sensor.

Figure 14A:
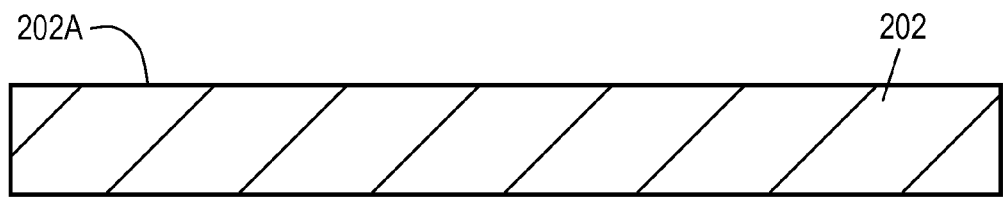
FIG. 14A is a sectional view of the localized plasmon resonance sensor shown in FIG. 13A for illustrating a method of manufacturing the sensor.
Figure 14B:
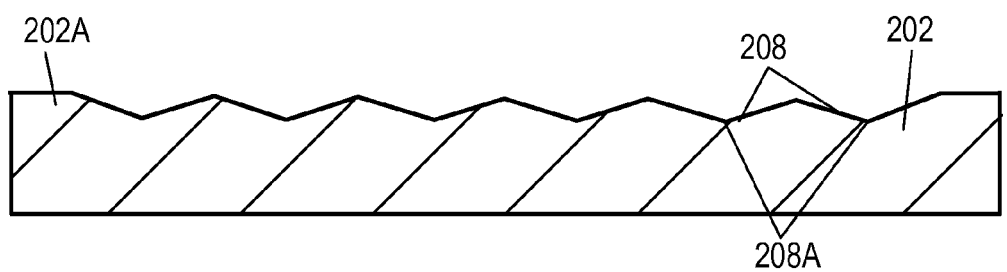
FIG. 14B is a sectional view of the localized plasmon resonance sensor shown in FIG. 13A for illustrating the method of manufacturing the sensor.
Figure 14C:
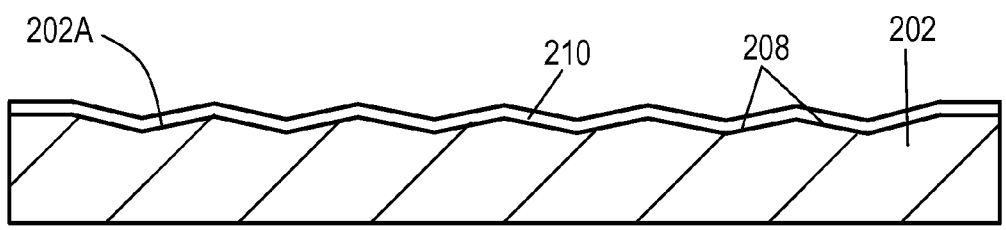
FIG. 14C is a sectional view of the localized plasmon resonance sensor shown in FIG. 13A for illustrating the method of manufacturing the sensor.
Figure 14D:
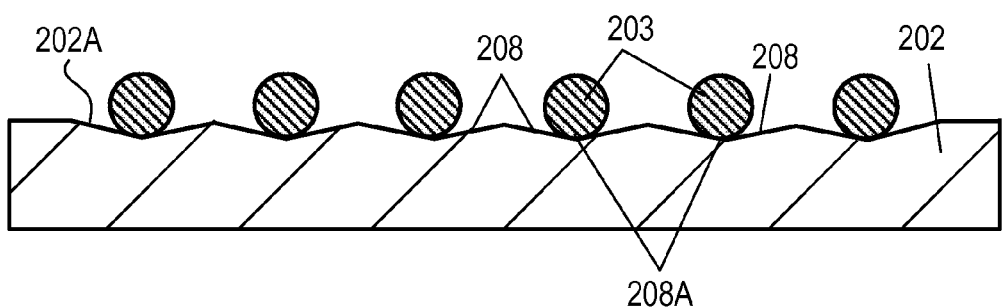
FIG. 14D is a sectional view of the localized plasmon resonance sensor shown in FIG. 13A for illustrating the method of manufacturing the sensor.

First, base 202 having surface 202A shown in FIG. 14A is prepared. Next, surface 202A of base 202 is dry-etched to form plural concave portions 208, as shown in FIG. 14B. Metal film 210 is then formed on surface 202A of base 202, as shown in FIG. 14C. Metal film 210 is made of metal, such as gold or silver. Subsequently, metal film 210 is heated to melt while surface 202A is directed upward and cohering the metal on bottom surfaces 208A of concave portions 208, thereby forming metal particles 203, as shown in FIG. 14D. Metal film 210 may be heated simultaneously to heating base 202. After that, probes 204 are fixed to surfaces 203A of metal particles 203, as shown in FIG. 13A, providing localized plasmon resonance sensor 209.

In localized plasmon resonance sensor 301 shown in FIG. 13B, probes 204 may be fixed not only to surfaces 203A of metal particles 203 but also to the entire surface 202A of base 202, similarly to localized plasmon resonance sensor 209 shown in FIG. 13A. This structure allows the localized plasmon resonance sensor to be manufactured by with simple processes.

Localized plasmon resonance sensor 201 shown in FIG. 12 can be manufactured by skipping the process shown in FIG. 14B out of the processes shown in FIGS. 14A to 14D.

Figure 15:
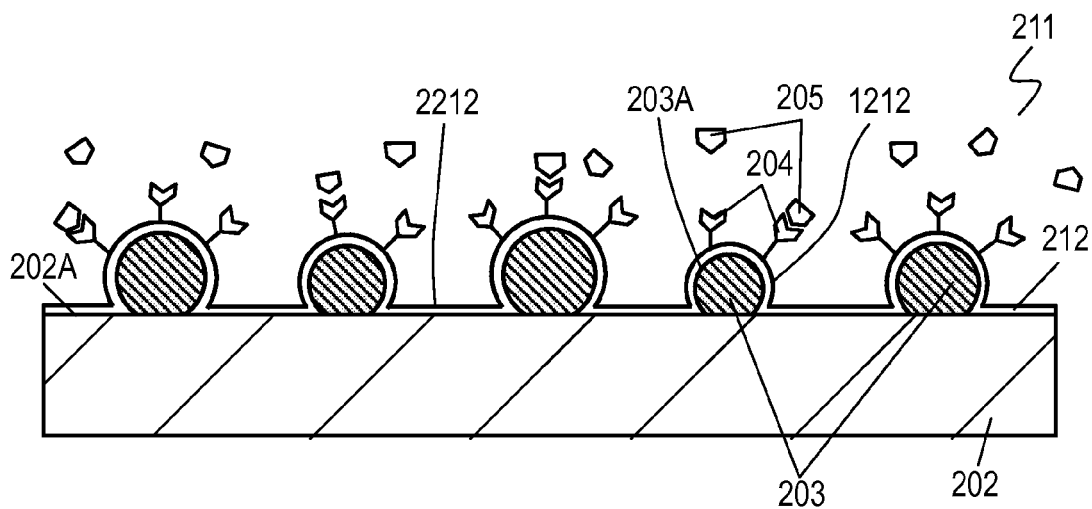
FIG. 15 is a sectional view of a further localized plasmon resonance sensor according to Embodiment 3.

FIG. 15 is a sectional view of further localized plasmon resonance sensor 211 according to Embodiment 3. In FIG. 15, components identical to those of localized plasmon resonance sensor 201 shown in FIG. 12 are denoted by the same reference numerals. Localized plasmon resonance sensor 211 further includes dielectric film 212 having a high nonlinear optical effect provided between metal particles 203 and probes 204. Dielectric film 212 is formed on surfaces 203A of metal particles 203 as well as on surface 202A of base 202. Thus, dielectric film 212 has portions 1212 covering surfaces 203A of metal particles 203 and portion 2212 covering surface 202A of base 202. Probes 204 are fixed to at least portions 1212 of dielectric film 212. Dielectric film 212 is made of lead perovskite-type material or non-lead inorganic nonlinear optical material. Any of these materials has a high nonlinear optical effect, and provides localized plasmon resonance sensor 211 with high sensitivity similarly to localized plasmon resonance sensors 1, 101 and 701 to 705 according to Embodiments 1 and 2. Dielectric film 212 improves heat resistance of localized plasmon resonance sensor 211, accordingly allowing localized plasmon resonance sensor 211 to be manufactured easily.

Figure 16:
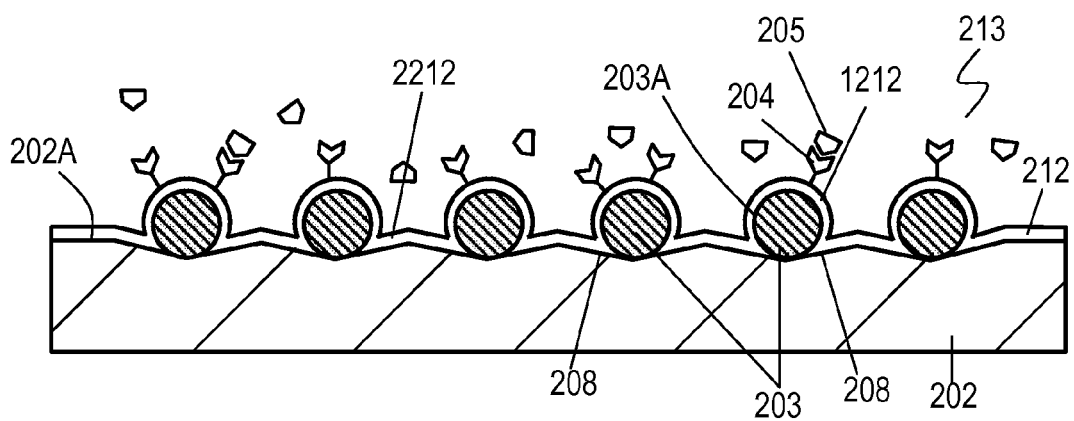
FIG. 16 is a sectional view of a further localized plasmon resonance sensor according to Embodiment 3.

FIG. 16 is a sectional view of further localized plasmon resonance sensor 213 according to Embodiment 3. In FIG. 16, components identical to those of localized plasmon resonance sensor 209 shown in FIG. 13A are denoted by the same reference numerals. Localized plasmon resonance sensor 213 shown in FIG. 16 includes dielectric film 212 having a nonlinear optical effect formed between metal particles 203 and probes 204 of localized plasmon resonance sensor 209 shown in FIG. 13A. Dielectric film 212 is formed on surfaces 203A of metal particles 203 as well as on surface 202A of base 202. Dielectric film 212 is made of lead perovskite-type material or non-lead inorganic nonlinear optical material. Any of these materials has a high nonlinear optical effect, and provides localized plasmon resonance sensor 213 with high sensitivity, similarly to localized plasmon resonance sensors 1, 101 and 701 to 705 according to Embodiments 1 and 2. Dielectric film 212 improves heat resistance of localized plasmon resonance sensor 213, accordingly allowing localized plasmon resonance sensor 213 to be manufactured. Furthermore, metal particles 203 have shapes substantially identical to each other and arranged regularly with constant intervals on surface 202A of base 202. This arrangement of metal particles 203 can reduce variations in the resonance frequency for generating a plasmon resonance in localized plasmon resonance sensor 213.

Dielectric film 212 of localized plasmon resonance sensor 213 shown in FIG. 16 can be formed on surface 202A of base 202 and surfaces 203A of metal particles 203 by the sputtering method after the process shown in FIG. 14D. In this case, dielectric film 212 may be formed on surface 202A of base 202 and surfaces 203A of metal particles 203 by the sputtering method after metal particles 203 are formed by heating base 202 shown in FIG. 14C to melt metal film 210 and cohering it, but before the temperature of base 202 is lowered to a ordinary temperature, such as a room temperature. These processes can reduce an amount of energy necessary for manufacturing localized plasmon resonance sensor 213. These processes can also form dielectric film 212 of localized plasmon resonance sensor 211 shown in FIG. 15, providing the same effects.

Figure 17:
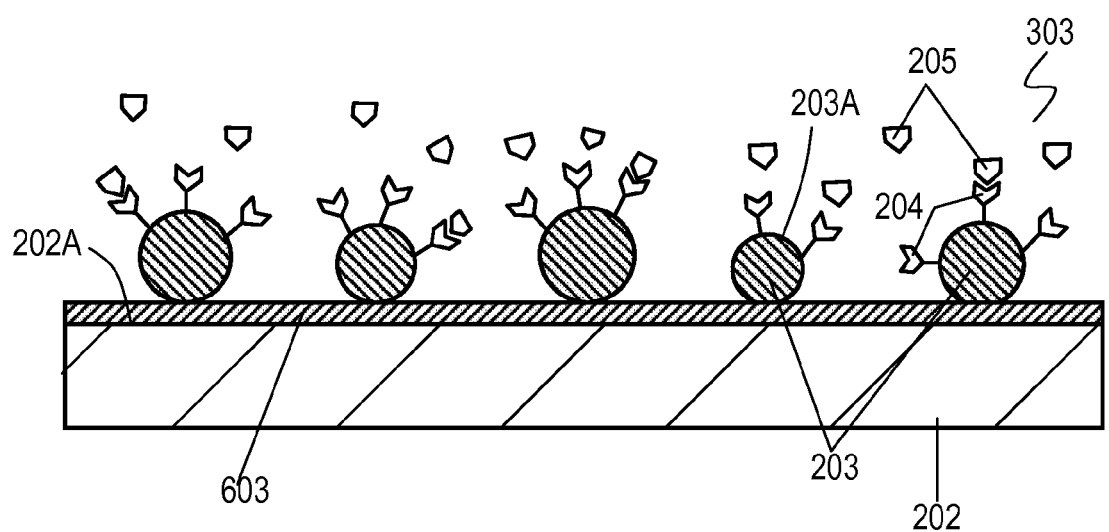
FIG. 17 is a sectional view of a further localized plasmon resonance sensor according to Embodiment 3.

FIG. 17 is a sectional view of further localized plasmon resonance sensor 303 according to Embodiment 3. In FIG. 17, components identical to those of localized plasmon resonance sensor 201 shown in FIG. 12 are denoted by the same reference numerals. In localized plasmon resonance sensor 303 shown in FIG. 17, titanium layer 603 is disposed between surface 202A of base 202 and metal particles 203. That is, titanium layer 603 is disposed on surface 202A of base 202, and metal particles 203 are formed on titanium layer 603. Metal particles 203 have strong adhesion to titanium layer 603, and hence, adhere strongly to base 202. Localized plasmon resonance sensors 209, 211, 213, 301 and 302 according to Embodiment 3 shown in FIGS. 13A to 16 may include a titanium layer similar to titanium layer 603 shown in FIG. 17 between surface 202A of base 202 and metal particles 203, providing the same effects.

The surfaces of concave portions 208 shown in FIG. 13A and FIG. 16 may be rougher than the surfaces other than concave portions 208 of base 202. This structure increases the strength of adhesion of metal particles 203 to concave portions 208 in surface 202A of base 202.

In localized plasmon resonance sensors 201, 209, 211, 213, 301 and 302 according to Embodiment 3 shown in FIGS. 12 to 16, probes 204 are disposed on surfaces 203A of metal particles 203 or dielectric film 212, i.e., are near metal particles 203.

The localized plasmon resonance sensors according to Embodiments 1 to 3 measure antigen-antibody reactions and hybridization of nucleic acids.

INDUSTRIAL APPLICABILITY

A localized plasmon resonance sensor according to the present invention has high measurement sensitivity, and is useful as sensors for accurately measuring a reaction, such as antigen-antibody reactions and hybridization of nucleic acid, of a probe coupled with object substance.

REFERENCE MARKS IN THE DRAWINGS

3 Substrate
5 Dielectric Film
6 Probe
8 Object Substance
102 Convex Portion
102A Convex Portion
103 Substrate
105 Dielectric Film
106 Probe
107 Object Substance
109 Concave Portion
110 Base
111 Pit
202 Base
203 Metal Particle
204 Probe
205 Object Substance

The invention claimed is:

1. A surface plasmon resonance sensor comprising:
a substrate having a first surface and a second surface opposite to the first surface, the substrate being made of metal;
a dielectric film provided on the first surface of the substrate, the dielectric film having a nonlinear optical effect; and
a probe fixed to the dielectric film,
wherein a plasmon resonance is produced by resonating a surface plasmon generated on the first surface of the substrate with an evanescent wave generated on the second surface of the substrate by incident light radiated to the second surface, and
wherein the plasmon resonance is detected by measuring a change of a component of light reflected on the second surface of the substrate, the component of the reflected light being caused by the nonlinear optical effect.

2. The surface plasmon resonance sensor according to claim 1, wherein the dielectric film is made of lead perovskite-type material or non-lead inorganic nonlinear optical material.

3. The surface plasmon resonance sensor according to claim 1,
wherein the incident light has a vibration frequency ω, and
wherein the component of the reflected light has a frequency nω, where n is an integer larger than one.

4. A localized plasmon resonance sensor comprising:
a substrate including a convex portion having a convex surface and an opposite surface opposite to the convex surface, the substrate being made of metal;
a dielectric film provided on at least one of the convex surface and the opposite surface of the convex portion, the dielectric film being made of lead perovskite-type material or non-lead inorganic nonlinear optical material, the dielectric film having a nonlinear optical effect; and
a probe fixed to the dielectric film, the probe specifically being coupled with an object substance,
wherein the convex portion is irradiated with incident light for exciting localized plasmon on the convex portion, and
wherein the localized plasmon resonance sensor detects that the probe is coupled with the object substance by measuring light radiated due to the nonlinear optical effect of the dielectric film.

5. The localized plasmon resonance sensor according to claim 4, wherein the opposite surface of the substrate comprises a concave surface protruding in a same direction as the convex surface.

6. A method of manufacturing a localized plasmon resonance sensor, comprising:
forming a pit in a surface of a base;
forming a substrate made of metal on the pit and the surface of the base, the substrate having a convex portion located in the pit;
forming a dielectric film made of lead perovskite-type material or non-lead inorganic nonlinear optical material on the substrate; and
providing a probe on the dielectric film, the probe being configured to be coupled specifically with an object substance,
wherein the convex portion is irradiated with incident light for exciting localized plasmon on the convex portion, and
wherein the localized plasmon resonance sensor is configure to detect that the probe is coupled with the object substance by measuring light radiated due to the nonlinear optical effect of the dielectric film.

7. The method according to claim 6, further comprising removing the base after said forming of the substrate.

* * * * *